United States Patent

Gonze et al.

Patent Number: 6,083,438
Date of Patent: Jul. 4, 2000

[54] TABLETTING OF ERYTHRITOL

[75] Inventors: Michel Henri André Gonze, Brussels; Jean-Claude Marie-Pierre Ghislain De Troostembergh, Houwaart, both of Belgium

[73] Assignee: Cerestar Holding B.V., La Sas Van gent, Netherlands

[21] Appl. No.: 09/129,383

[22] Filed: Aug. 5, 1998

[30] Foreign Application Priority Data

Aug. 5, 1997 [GB] United Kingdom ............ 9716432

[51] Int. Cl.⁷ .................. B29C 43/02; B29B 13/04; B29B 13/02; B29B 9/02

[52] U.S. Cl. ............ 264/115; 264/122; 264/330; 426/658; 106/287.26

[58] Field of Search .............. 106/194.2, 287.23, 106/287.26; 426/658; 264/109, 115, 122, 125, 126, 330, 299

[56] References Cited

U.S. PATENT DOCUMENTS

| | | |
|---|---|---|
| 3,341,415 | 9/1967 | Scott . |
| 3,639,168 | 2/1972 | Monti et al. . |
| 5,043,169 | 8/1991 | Cherukuri et al. ............ 426/5 |
| 5,120,550 | 6/1992 | Van Der Schueren ........ 426/3 |
| 5,573,777 | 11/1996 | Serpelloni et al. ............ 424/440 |

FOREIGN PATENT DOCUMENTS

| | | |
|---|---|---|
| 487 774 | 6/1992 | European Pat. Off. . |
| 497 439 | 8/1992 | European Pat. Off. . |
| 509 606 | 10/1992 | European Pat. Off. . |
| 528 604 | 2/1993 | European Pat. Off. . |
| 97/39739 | 10/1997 | WIPO . |

*Primary Examiner*—Jan H. Silbaugh
*Assistant Examiner*—Kenneth M. Jones
*Attorney, Agent, or Firm*—Pillsbury Madison & Sutro LLP

[57] ABSTRACT

A process for preparing a composition suitable for use as an excipient for tabletting comprising the following steps is disclosed;

a) mixing of erythritol and sorbitol in a dry form,
b) heating up to a temperature where the mixed products are melted,
c) cooling the product,
d) milling the cooled product to obtain a composition having a desired particle size.

Additionally tablets obtained after direct compression of an erythritol/sorbitol mixture are disclosed.

4 Claims, 5 Drawing Sheets

TABLETTING OF ERYTHRITOL

TECHNICAL FIELD

The present invention relates to the preparation of a composition for tabletting. The tabletting is performed by direct compression of a blend of erythritol and a second polyol, specifically sorbitol. The mix of erythritol and the second polyol is obtained by co-crystallisation.

BACKGROUND OF THE INVENTION

Tablets for pharmaceutical, confectionery or food applications are mostly made with starch or sugar as excipients. The use of white starch for making tablets has been described in European patent EP 0 564 700.

Generally, starch products are relatively easy to compress and they give a tablet, which is easily soluble and has the required hardness. The tablet, which may contain as an active ingredient a pharmaceutical product, should readily disintegrate in water and in the gastrointestinal tract after being swallowed.

The tablet does not only contain the drug or a reagent, it also contains other ingredients which act as fillers, such as lactose or phosphates; lubricating agents, such as talc, stearic acid or paraffin and disintegrating agents, such as carboxymethyl-cellulose or starch. For confectionery purposes the tablets often include aroma's and colorants at low concentration.

With the present interest in the use of sugar-free and/or low calorie products, the use of starch-based and sugar excipients is seriously questioned. Sugar alcohols, such as xylitol, maltitol, sorbitol, mannitol and erythritol are already widely used for sugar replacement. Sugar alcohols have a much lower caloric content than sugar. The use of several sugar alcohols as excipients was extensively tested. Until now it has not been possible to use erythritol as a suitable excipient because compression resulted in a product which was much too brittle.

Direct compression of spray-dried erythritol has been described in European patent EP 0 497 439. The hardness of the product was found to be too low for normal application.

U.S. Pat. No. 3,341,415 by Scott, describes a process for preparing mannitol-based excipients. The process comprises the mixing of mannitol with a second sugar, heating the mixture and preferably congealing the mixture. The product is then used for tabletting. The mixture based on mannitol and erythritol gives rise to a tablet with a friability which is too high and a tensile strength which is too low for good application in tablets as illustrated by the examples of the invention which forms the subject of the present patent application.

U.S. Pat. No. 3,639,168 by Monti et al. describes the preparation of a direct compression vehicle by dispersing a diluant such as sugar, in a fully hydrated hydratable polymer, such as starch, drying the resulting dispersion, and reducing the dried product to particles of the desired size.

European patent application EP 0 528 604 discloses the co-crystallized sorbitol and xylitol and tablets made therefrom.

European patent application EP 0 509 606 relates to the production of tabletting excipients containing lactose, having a high β-lactose content.

Recently, it was described that erythritol is not only non-cariogenic but that it also has an anti-cariogenic activity. When starch, which is normally cariogenic is mixed with a sufficient amount of erythritol the product is non-cariogenic. This finding, which forms the subject of a co-pending patent application, only increases the interest in the use of erythritol as an excipient.

SUMMARY OF THE INVENTION

The present invention discloses tablets comprising erythritol and a second polyol, specifically sorbitol.

The present invention also describes a process for obtaining tablets comprising erythritol and sorbitol. The process comprises the direct compression of a composition obtained in a new way. The tablets show excellent friability and hardness.

The present invention further discloses a process for preparing a composition suitable for use as an excipient for tabletting comprising the following steps;

a) mixing of erythritol and sorbitol in a dry form, b) heating to a temperature where the mixed products are melted, c) cooling the product, d) milling the cooled product to obtain a composition having a desired particle size.

The preferred polyol for mixing with erythritol in a dry state is sorbitol.

DETAILED DESCRIPTION OF THE INVENTION

Figure 1:
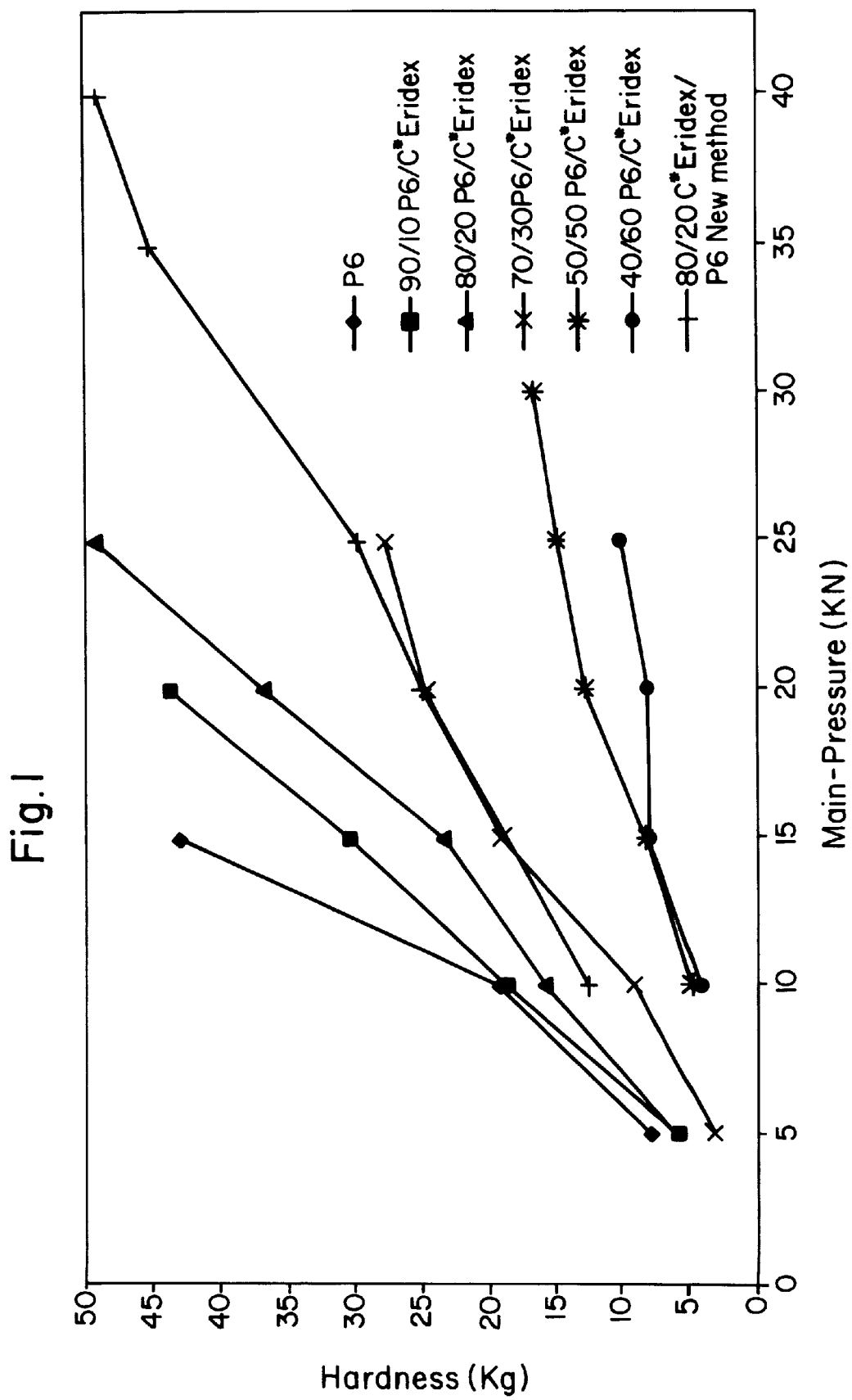
FIG. 1 shows the hardness (in Kg) of the tablets as a function of the pressure (KiloNewton, kN) for compositions containing different ratios of erythritol to sorbitol.

The present invention discloses tablets comprising erythritol as an excipient in combination with another polyol. The tablets of the present invention contain as a disintegrant a combination of erythritol and another polyol wherein the erythritol is present in an amount of between 50 and 90% (w/w) preferably between 60 and 80% (w/w). Particularly good results have been obtained when erythritol was mixed with sorbitol (Sorbidex P6).

It was shown in Example 1 that the use of a ratio of erythritol to sorbitol of 80% to 20% results in tablets having a hardness comparable to when tablets were made from a non-co-crystallized mixture of erythritol to sorbitol having a ratio of 30% to 70%.

The tablets having the composition of the present invention, and for which a preparation method is disclosed hereinafter show a hardness, friability and an ejection force which make them suitable for pharmaceutical and confectionery applications. The disintegration is sufficient whereas at the same time the tablets are not too brittle.

When comparing tablets made from different mixtures of polyols in a ratio of 80% erythritol to 20% other polyol, as shown in the second example, it appeared that the erythritol:sorbitol mixture (80:20 in this case), resulted in the best tablets as regards friability and hardness. These tablets are suitable when mixed with the desired ingredients to from the basis of pharmaceutical or confectionery products.

Example 2 shows the tabletting behaviour of the product obtained by co-crystallisation of erythritol with mannitol, sorbitol, maltitol and xylitol, respectively and in a ratio of 80 to 20. Comparison of the tested products as regards tensile strength, friability and ejection force clearly demonstrates that the preferred combination is erythritol with sorbitol. This combination results in tablets having the required hardness and friability.

Example 3 demonstrates the effect of the use of a Readco Continuous Processor made by Teledyne Readco of York, Pa. It is shown that the combination of erythritol and sorbitol (80:20) when prepared using a low rotation speed results in tablets having a hardness which equals that of pure sorbitol. It should be noted that the use of pure sorbitol is an accepted practice for making tablets.

The present invention further discloses as process for preparing a composition, which is used for preparing tablets. The process comprises the following steps;

a) mixing of erythritol and sorbitol in a dry form, b) heating to a temperature where the mixed products are melted, c) cooling the product, d) milling the cooled product to obtain a composition having a desired particle size.

Preferably the other polyol is sorbitol. The mixture of erythritol and the other polyol is heated to a temperature whereby the polyols are melted. The temperature is not increased to such a temperature as would negatively influence the polyols. Temperatures of up to 150° C. have been found to be applicable. During cooling of the mixture crystals are formed. The composition is then milled to obtain particles of a size that are suitable for direct compression. Suitable particle sizes are in the range of from 20 to 1000 micrometers.

The present invention also describes a process for obtaining tablets comprising erythritol. The process consists in direct compression of the composition obtained above i.e. mixing, heating, cooling and milling after having added the desired additional compounds.

The type and amount of additional compounds added depends on the application for which the tablets are prepared. If tablets are prepared for confectionery applications than in general up to about 99% (w/w) consists of the milled polyol mixture additionally aroma, colourant, flavour and a lubricating agent, are added. If tablets are prepared for pharmaceutical applications an active ingredient such as a drug is added and fillers, lubricating agents or disintegrating agents are added if needed. Depending on the type of compound added the addition may be done before the crystallisation i.e. before heating or during cooling alternatively addition may be done before during or after milling. It is further possible to add the ingredients before compression. Finally, it is possible to add the ingredients after compression for example in the form of a coating.

The invention will hereunder be illustrated in the form of a series of non-limiting examples.

EXAMPLE 1

Erythritol (available from Cerestar in crystalline form under the tradename C☆Eridex) was mixed with sorbitol (SORBIDEX) in a ratio of 80% to 20%. The mixture was heated to 140° C. and stand to cool to room temperature during which time the product crystallized. The product was milled with a Bauer Meister.

As a reference mixtures of dry erythritol and Sorbidex P6 were mixed in different ratios without any further treatment.

The compositions were compressed using a pressure of between 5 and 35 kiloNewton on a Fette P1000 tabletting machine. The hardness of the product was measured in a Fette 'Checkmaster 3', the results are presented in FIG. 1. It can be seen that the hardness of a mixture of 80% erythritol and 20% Sorbidex P6 treated according to the present invention has a hardness comparable with an untreated mixture of 70% Sobidex P6 and 30% erythritol.

By varying the ratio of erythritol to sorbitol the hardness can be adapted to a desired value.

EXAMPLE 2

The method of Example 1 was used to investigate the tabletting behaviour of the product obtained by co-crystallisation of erythritol with mannitol, sorbitol, maltitol and xylitol in a ratio of 80 to 20. The tested products were:

Erythritol/Mannitol (80/20)
Erythritol/Sorbitol (80/20)
Erythritol/Maltitol (80/20)
Erythritol/Xylitol (80/20)

Size analysis was performed using a sieve of 0.8 mm. For each batch a formulation containing 1% MgSt and 0.25% SiO2 was prepared and compressed into tablets (1 cm$^2$ surface/350 mg) at compression forces ranging from 5 kN to 30 kN at a speed of 40 rpm.

Hardness

Figure 2:
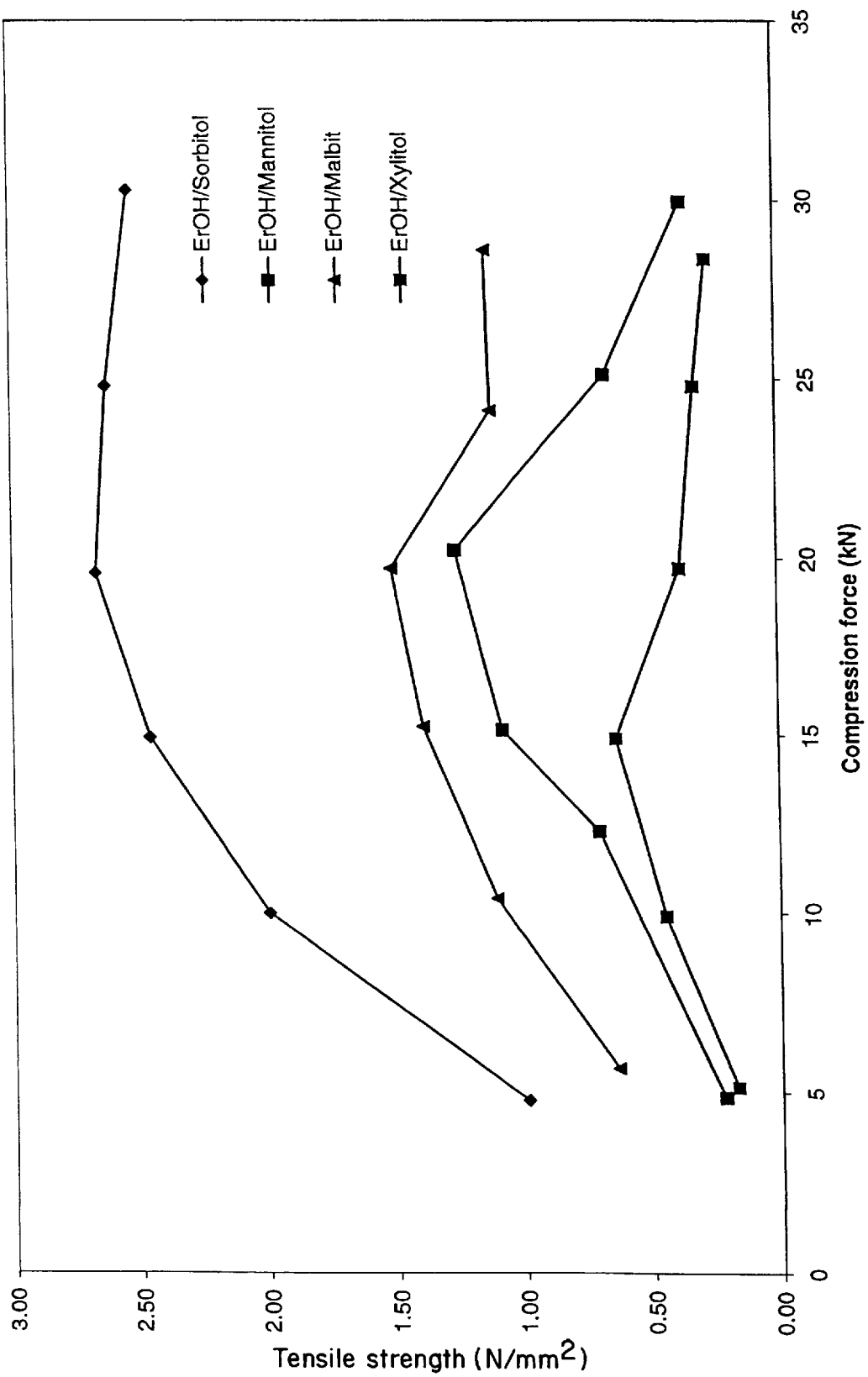
FIG. 2 shows the tensile strength (N/mm2) as a function of the compression force (kN).

FIG. 2 shows the tensile strength as a function of the compression force. It can be concluded that only the erythritol/sorbitol mixture gives acceptable tablets. At higher compression forces the tensile strength slightly decreases, in all cases, this indicates capping. For the other polyol combinations the tensile strength is not sufficiently high and the tendency of capping is even more pronounced.

Friability

Figure 3:
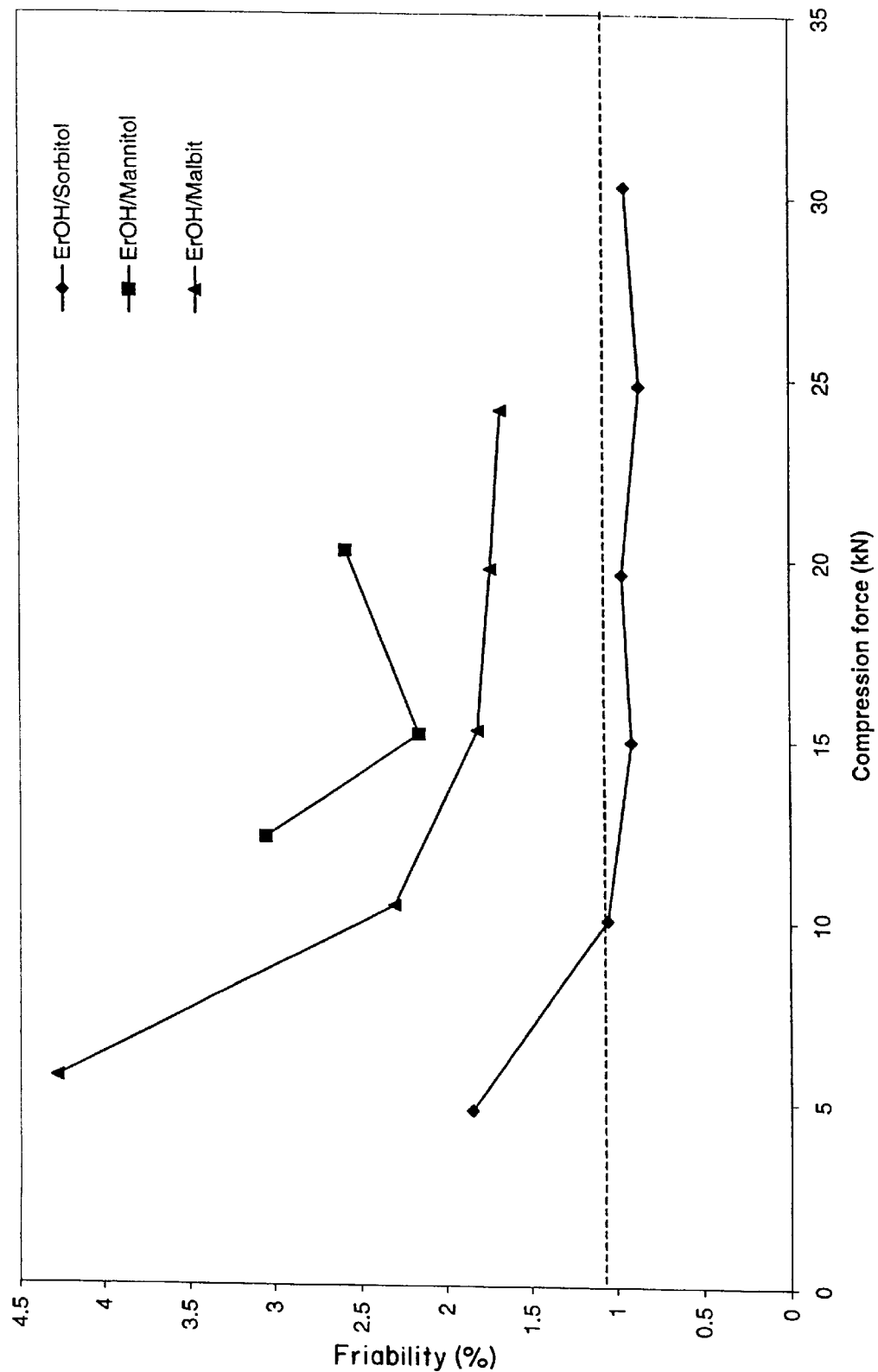
FIG. 3 shows the friability as a function of the compression force (kN).

The friability as a function of the compression force is shown in FIG. 3. It can be concluded that only the tablets of the co-crystallised erythritol/sorbitol meet the pharmacopoeial limit of 1%. For erythritol/xylitol is was not even possible to measure the friability, because of the too soft tablets.

Ejection Force

Figure 4:
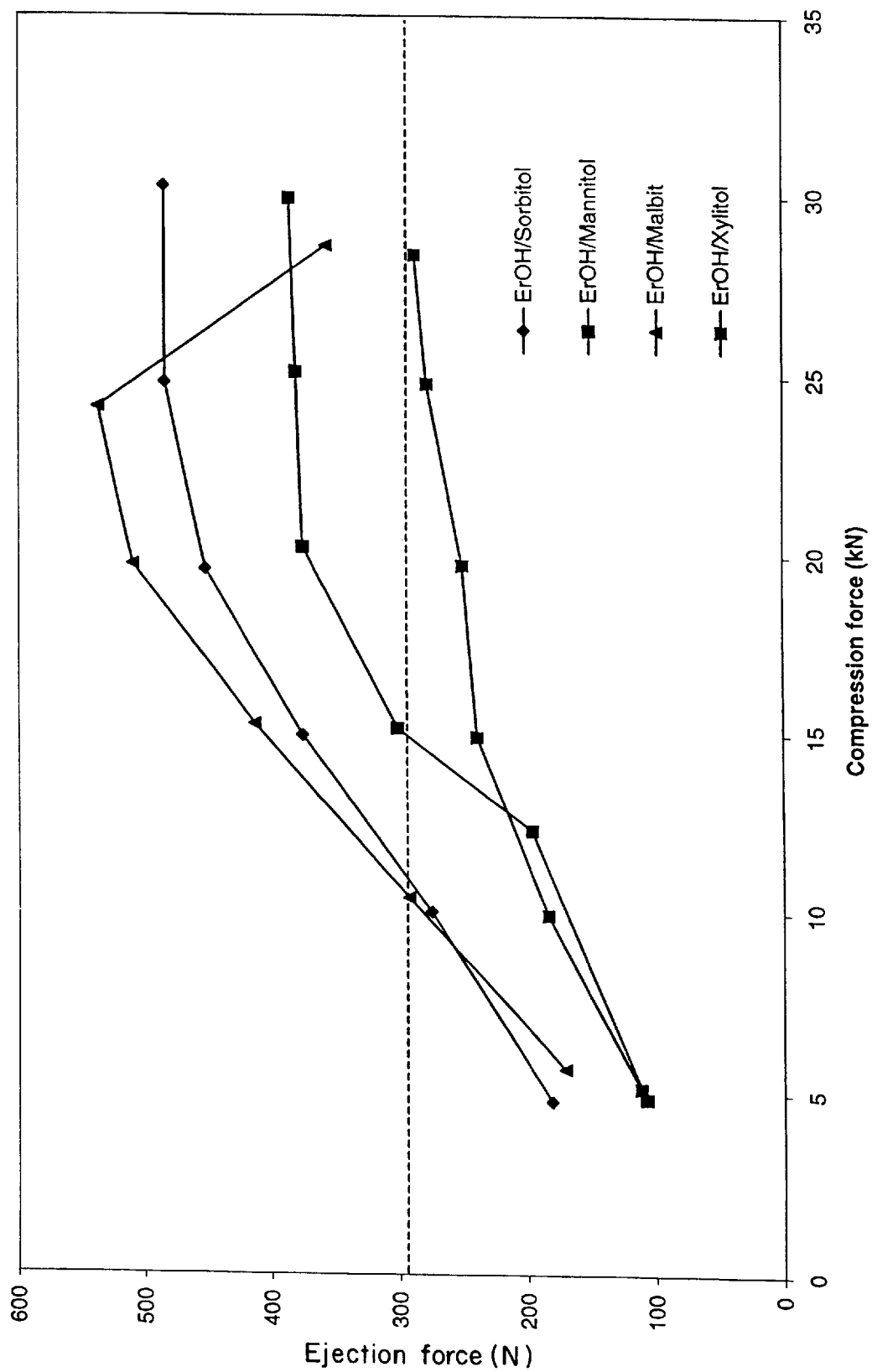
FIG. 4 shows the ejection force (N) as a function of the compression force (kN).

FIG. 4 shows the ejection force as a function of the compression force. The maximum allowed ejection force by the pharmacopoeia is 300 N, which is exceeded by all four products at higher compression forces. The reason for this is the elastic recovery after compression.

EXAMPLE 3

A 80:20% blend of erythritol and sorbitol was tested in direct compression experiments. The mixture was extruded using different rotating speeds of the Readco continuous mixer, as shown in Table 1.

Typically, a melt of erythritol and sorbitol was heated to slightly above the melting point (125° C.) and fed to the Readco continuous mixer. The mixer from Teledyne Readco company of York, Pa. had a length of 91.4 cm, a nominal diameter of 12.7 cm, dual mixer blade shafts, a heat exchanger surface area of about 0.56 m2 and a nominal power of 7.5 kW. The operating conditions of the run included a shaft rotation speed as indicated in Table 1. The melt throughput was between 50 kg/hr and the jacket cooling was at 14–18° C.

TABLE 1

Erythritol/sorbitol (80:20%) blends prepared at given rotation speed.

|  | KR 8953 | KR 8954 | KR 8955 |
|---|---|---|---|
| Rotation speed | 28 rpm | 40 rpm | 80 rpm |
| Flow rate | 50 kg/h | 50 kg/h | 50 kg/h |
| Water content % | 0.23% | 0.22% | 0.27% |

The slightly higher water content of KR 8955 should result in a somewhat higher hardness. In the present case this does however not influence the outcome.

Figure 5:
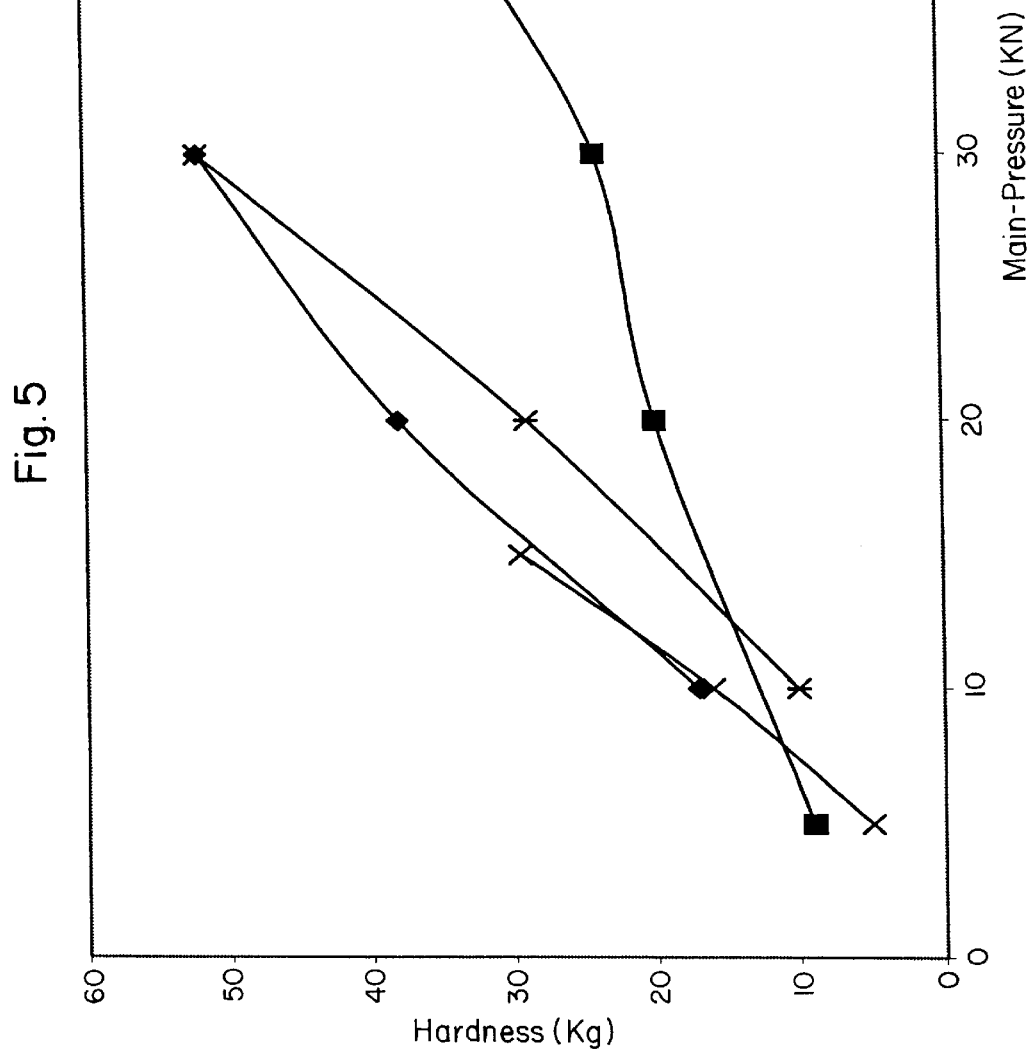
FIG. 5 shows the hardness (in Kg) of the tablets as a function of the pressure (KiloNewton, kN) for compositions containing different ratios of erythritol to sorbitol, and pure sorbitol (SORBIDEX® P16616, available from Cerestar)

Tablets were prepared by mixing 1% of Mg stearate with 99% of the blends of Table 1 during 3 minutes. The resulting tablets were tested for hardness. The results of this test are given in FIG. 5. It appears that the tablets from KR 8953 have a hardness which is almost identical with that of pure sorbitol.

What is claimed is:

1. A process for preparing a composition suitable for use as an excipient for tabletting comprises the following steps:
    a) mixing polyols to form a mixed product wherein said polyols are in a dry form and wherein the polyols consist of erythritol and sorbitol,
    b) heating said mixed product to a temperature where the mixed product is melted to form a melted product,
    c) cooling the melted product to form a solidified, cooled product,
    d) milling the cooled product to obtain a composition having a desired particle size.

2. A process according to claim 1 wherein said erythritol and sorbitol are present in a ratio of 50% to 50% to 90% to 10% dry weight.

3. A process according to claim 1 characterised in that further ingredients are added during one of the steps a) to d).

4. A process for preparing a tablet comprising the following steps:
    a) mixing polyols to form a mixed product wherein said polyols are in a dry form and wherein the polyols consist of erythritol and sorbitol,
    b) heating said mixed product to a temperature where the mixed product is melted to form a melted product,
    c) cooling the melted product to form a solidified, cooled product,
    d) milling the cooled product to obtain a composition having a desired particle size,
    e) adding at least one other compound comprising pharmaceutical ingredients, disintegrants, colourants, fillers, lubricant or flavour to said composition to form a tablet mixture,
    f) compressing said tablet mixture to form a tablet.

* * * * *